United States Patent [19]

Hardy et al.

[11] Patent Number: 5,307,812
[45] Date of Patent: May 3, 1994

[54] HEAT SURGERY SYSTEM MONITORED BY REAL-TIME MAGNETIC RESONANCE PROFILING

[75] Inventors: Christopher J. Hardy; Harvey E. Cline, both of Schenectady, N.Y.

[73] Assignee: General Electric Company, Schenectady, N.Y.

[21] Appl. No.: 38,204

[22] Filed: Mar. 26, 1993

[51] Int. Cl.$^5$ ............................................. A61B 5/055
[52] U.S. Cl. ..................... 128/653.2; 128/736; 607/89; 607/97; 606/15; 601/2
[58] Field of Search ............... 128/653.2, 736, 24 AA, 128/653.5, 804; 607/88, 89, 96, 97; 324/315, 309; 606/2, 3, 11, 14–16

[56] References Cited

U.S. PATENT DOCUMENTS

| | | | |
|---|---|---|---|
| 4,554,925 | 11/1985 | Young | 128/653.2 |
| 4,914,608 | 4/1990 | Le Bihan et al. | 128/653.2 X |
| 4,951,688 | 8/1990 | Keren | 128/804 |
| 5,109,853 | 5/1992 | Taicher et al. | 128/653.2 |
| 5,247,935 | 9/1993 | Cline et al. | 128/653.2 |

Primary Examiner—Ruth S. Smith
Attorney, Agent, or Firm—Lawrence P. Zale; Marvin Snyder

[57] ABSTRACT

Surgery is performed with a pulsed heat-producing device that selectively heats a region in a specific tissue within a patient destroying the tissue. The pulsed heat-producing device may be a coherent optical source that is guided by laser fiber to the tissue to be destroyed. In another embodiment, the pulsed heat-producing device is a focussed ultrasound transducer which concentrates ultrasonic energy at a focal point within the specific tissue. A magnetic resonance imaging system employing a real-time temperature-sensitive pulse sequence monitors the heated region of the tissue to provide temperature profiles allowing an operator to alter the position and size of the heated region.

7 Claims, 14 Drawing Sheets

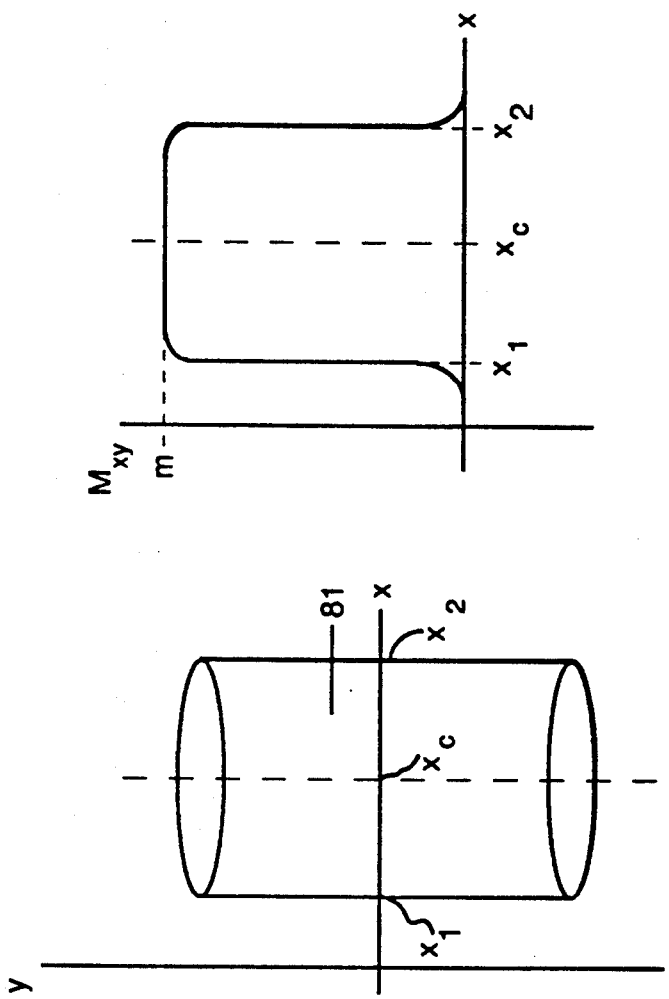
*Fig. 8b*
*Fig. 8a*
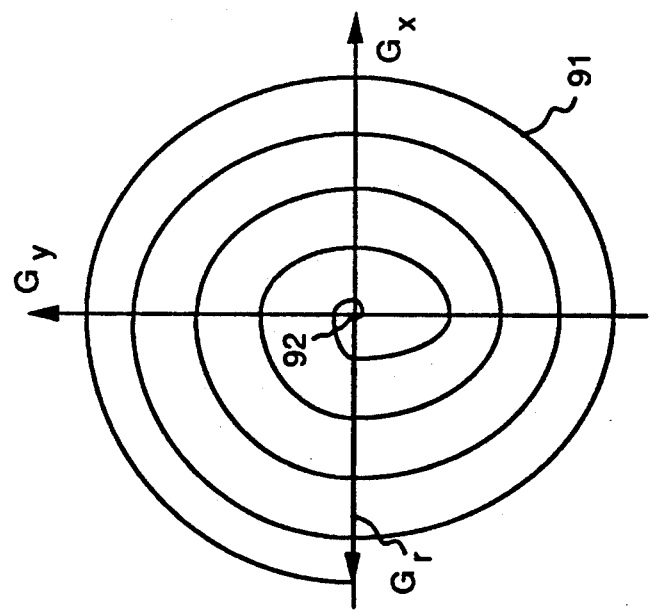
*Fig. 6*

HEAT SURGERY SYSTEM MONITORED BY REAL-TIME MAGNETIC RESONANCE PROFILING

CROSS REFERENCE TO RELATED APPLICATION

This application is related to U.S. Pat. No. 5,247,935 issued Sep. 28, 1993 "Magnetic Resonance Guided Focussed Ultrasound Surgery" by Harvey Cline, Robert Ettinger, Kenneth Rohling and Ronald Watkins, U.S. patent application, "Magnetic Resonance Surgery Using Heat Waves Produced with A Laser Fiber or Focussed Ultrasound" by Harvey E. Cline and Thomas R. Anthony et al. Ser. No. 07/751,259 filed Aug. 29, 1991 and U.S. Pat. No. 5,133,357 issued Jul. 28, 1992 "Quantitative Measurement of Blood Flow Using Cylindrically Localized Fourier Velocity Encoding" by Charles L. Dumoulin, Christopher J. Hardy, Steven P. Souza, and Steven A. Ash all assigned to the present assignee and hereby incorporated by reference.

BACKGROUND OF THE INVENTION

The present invention relates to surgery performed by local heating guided by magnetic resonance (MR) imaging, and more particularly to a method and apparatus for performing surgery by pulsed local heating guided by real-time temperature-sensitive MR imaging.

Conventional MR imaging provides an operator, such as a surgeon or a radiologist, with internal views of a patient's anatomy. MR imaging provides excellent contrast between different tissues and is useful in planning surgical procedures. Many tissues in a patient such as a tumor, are much more visible in an MR image than as seen in actual surgery. The tumor can also be obscured by blood during surgery further reducing visibility.

Experiments on living tissue show that a heated zone above a critical temperature destroys tissue. This zone increases in size with time as the heat is applied to reach a steady state of both temperature and heat flow. If the maximum temperature is limited, then an area heated to a temperature exceeding the critical temperature causing destruction of tissue, approaches a predetermined size.

Researchers at Brigham and Womens Hospital, Boston, Mass. have proposed treatment of deep lying tumors by laser surgery, as described in "MR Imaging of Laser-Tissue Interactions", by F. A. Jolesz, A. R. Bleire, P. Jakob, P. W. Ruenzel, K. Huttl, G. J. Jako, Radiology 168:249 (1989).

In laser surgery of the brain, a small burr hole is drilled in the skull and a hollow needle containing an optical fiber is then inserted into the tumor. Optical energy is passed through the optical fiber and into the tumor heating the tumor. Lasers guided through fiber optics are potentially very useful for surgery in the brain, since they allow access (through biopsy needles) to deeply buried pathology with minimal disruption of intervening tissue. The laser destroys the pathological tissue through localized heating.

A view of the heated region is provided with the use of MR temperature-sensitive pulse sequences. One known MR temperature-sensitive pulse sequence is described in U.S. Pat. No. 4,914,608 "In-vivo Method for Determining and Imaging Temperature of an Object/Patient from Diffusion Coefficients Obtained by Nuclear Magnetic Resonance", by Denis LeBihan, Jose Delannoy, and Ronald L. Levin issued, Apr. 3, 1990. This sequence causes full MR images to be created. It is, therefore, relatively slow, time-consuming and not capable of monitoring quickly changing temperatures.

In focussed ultrasound surgery, acoustic energy is concentrated at a focal point within the tumor. The focussed acoustic energy causes heating of tissue at the focal point.

Tumors have been selectively destroyed in cancer patients using focussed ultrasound to heat tissue within the patient at the University of Arizona as reported in "Effects of Physical Parameters on High Temperature Ultrasound Hyperthermia" by B. E. Ballard, K. Hynynen and Robert. B. Roemer, Ultrasound in Med. & Biol. Vol. 16, No. 4, pp. 409–420, 1990. Billard et al. disclose that the control of heat is improved by using short heating pulses where the effect of blood perfusion is negligible. However, since they do not image the temperature distribution, it is difficult to hit small, deep laying targets.

It would be beneficial to accurately image, in real time, localized heating and selectively destroy a specific tissue with minimal invasiveness without harming surrounding healthy tissue.

OBJECTS OF THE INVENTION

It is an object of the present invention to selectively heat tissue of a patient with a small degree of invasiveness and accurately monitor the heated tissue in real time with magnetic resonance imaging.

It is another object of the present invention to accurately destroy selected tissue without harming surrounding tissue with a non-invasive procedure employing real-time magnetic resonance temperature-sensitive imaging.

SUMMARY OF THE INVENTION

In accordance with the preferred embodiment, a pulsed heat source concentrates heat at an application point. A positioning means, operated by an operator, such as a radiologist or surgeon, positions the application point to selectively heat specific tissue of a patient with minimal invasiveness. A magnetic resonance (MR) imaging device employs a real-time temperature-sensitive MR pulse sequence to create real-time temperature-sensitive images of the heated tissue which are provided to the operator performing the procedure. The operator then interactively adjusts the amount of heat concentrated at the application point and the position of the application point to selectively destroy the specific tissue.

The temperature-sensitive real-time MR pulse sequence causes an elongated region of magnetization to be excited within a specific tissue of the patient, employing a cylindrical excitation, or excitation of the intersection of two imaginary slices. The excited tissue emits an MR response signal which is temperature encoded by with a $T_1$-weighted readout gradient, or diffusion of magnetic field gradients. A one-dimensional Fourier transformation (1 DFT) is applied to the MR response signal to generate a magnetization profile. This profile indicates the temperature of tissue along the length of the excitation region. The excitation region is oriented to intersect tissue at the application point, thereby permitting real-time monitoring of heat destruction of the tissue.

BRIEF DESCRIPTION OF THE DRAWINGS

The features of the invention believed to be novel are set forth with particularity in the appended claims. The invention itself, however, both as to organization and method of operation, together with further objects, may best be understood by reference to the following description taken in conjunction with the accompanying drawing in which:

FIG. 6 is a graphical representation of a resultant magnetic-field gradient vector $G_r$, and its trajectory over time during cylindrical excitation.

FIG. 8a is a graphical illustration of the shape of a region of tissue excited by cylindrical-selection pulses.

FIG. 8b is a illustration of a cross-section of transverse magnetization of the region of FIG. 8a.

FIG. 14b is a position vs. time temperature-sensitive image being a continuation of FIG. 14a.

DETAILED DESCRIPTION OF THE INVENTION

A specific tissue, such as tumor tissue, in a patient may be selectively destroyed by localized heating without affecting the surrounding healthy tissue. A method of controlling the size of a region being heated by pulsing a heat source is disclosed in "Thermal Diffusity of Isotopically Enriched $^{12}C$ Diamond" by T. R. Anthony, W. F. Banholzer, and J. F. Fleischer Phys. Rev. B Vol. 42, No. 2 Jul. 15, 1990, hereby incorporated by reference. Similarly, in the present invention heat is applied to create a heated region in the tumor tissue in a pulsed or oscillating fashion. This oscillation creates a heat wave at an application point. The pulsed heat may be produced by a focussed ultrasound transducer or a laser and fiber optics. (A more detailed description of the heating profile of the ultrasound transducer is included in the aforementioned patent application Ser. No. 07/854,040). The heated region is monitored with a magnetic resonance (MR) imaging system employing a temperature-sensitive real-time MR pulse sequence. Images of internal structures of the patient and the heated regions are supplied to an operator allowing the operator to interactively adjust the position and size of the heated region.

Figure 1:
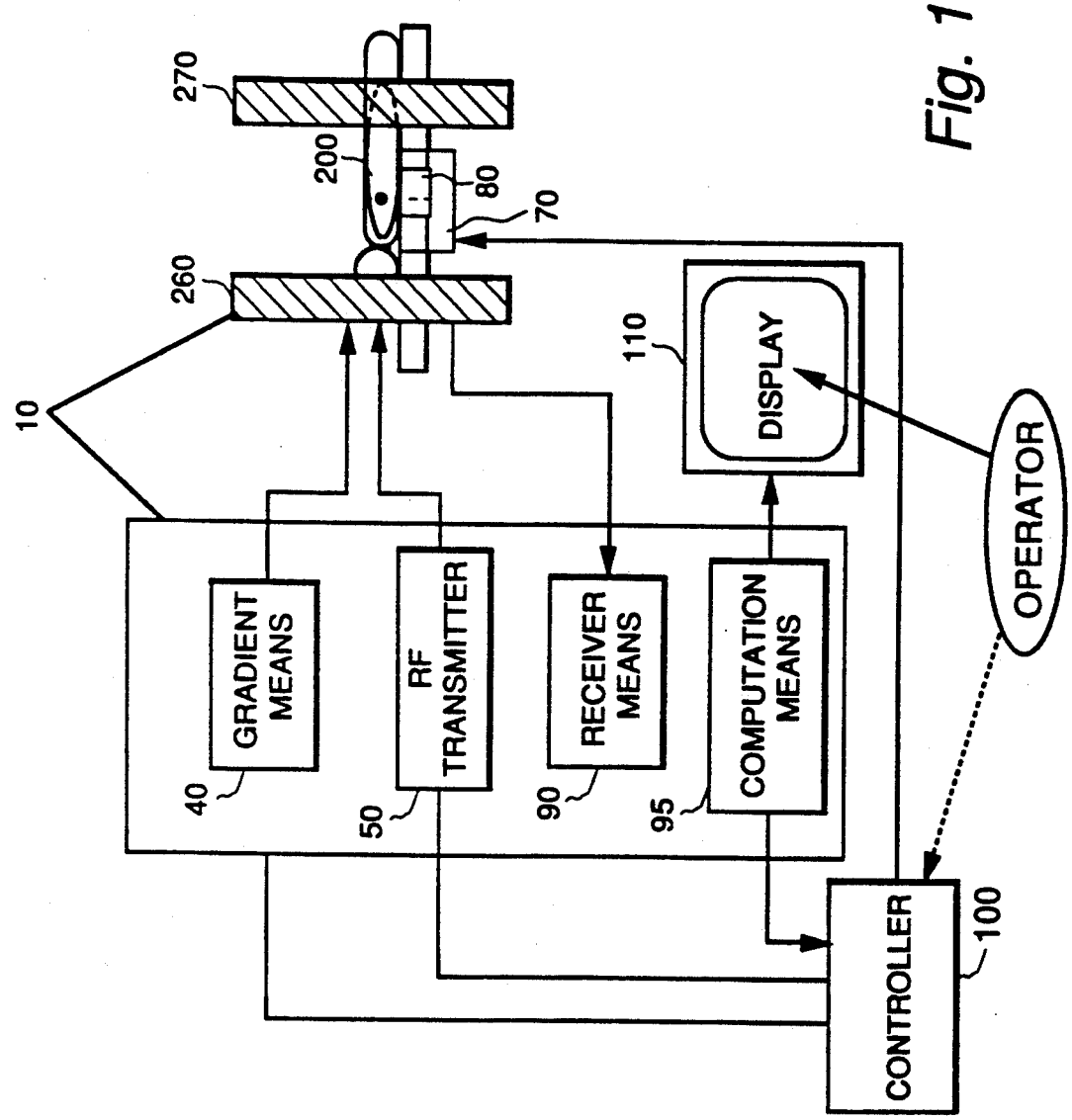
FIG. 1 is a block diagram of a magnetic resonance (MR) pulsed heat system according to the present invention.

A block diagram of the MR pulsed heat system of the present invention is shown in FIG. 1. An MR imaging device 10 comprises a static field magnet 260, 270, a gradient amplifier 40, an RF transmitter 50, a receiver 90 and a computation unit 95 which rapidly acquire images of a patient 200. Static field magnet 260, 270 provides a static magnetic field $B_0$ over patient 200 required for MR imaging. Gradient amplifier 40 and RF transmitter 50 supply the necessary magnetic field gradients and RF radiation, respectively, according to MR pulse sequences over patient 200 causing portions of patient to emit an MR response signal. Raw MR response signals are sensed by receiver 90 and passed to a computation unit 95 which computes an MR image. Computation unit 95 may then display images to an operator on a display 110. A controller 100 receives MR images from computation unit 95. The operator interfaces with controller 100 to compute a path from pulsed heat means to a desired location within patient 200 which avoids obstructions such as bone and air spaces within patient 200. In the case of brain tumors, a conventional MR image is acquired to locate the tumor and plan a safe trajectory between an entry point and target point within the tumor.

Controller 100 then actuates positioner 70 to position pulsed heat means 80. MR imaging device 10 employs real-time temperature-sensitive pulse sequences to rapidly acquire temperature-sensitive images of patient 200 which may optionally be superimposed on another medical diagnostic image (which may be the conventional MR image). Since both the internal structures and heated regions are imaged, the operator can accurately position the heated region to correspond to a desired internal structure, and accurately heat specific tissue.

Figure 2:
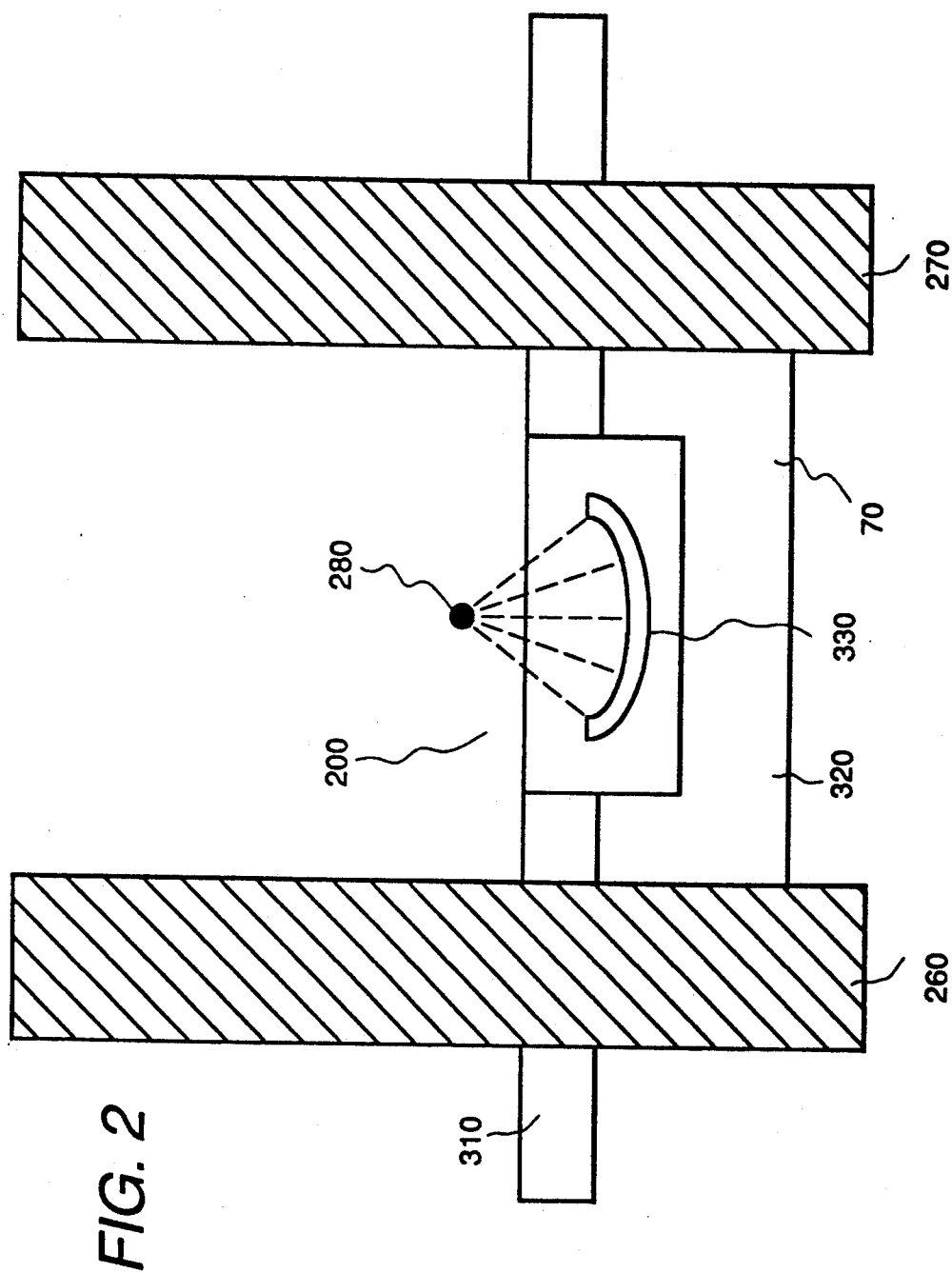
FIG. 2 is a partial illustration of a first embodiment of the present invention employing focussed ultrasound as a pulsed heat device with a patient positioned for surgery within the bore of the magnets.

A first embodiment of the MR pulsed heat system according to the present invention employing a focussed ultrasound transducer as the pulsed heat means 80 is shown in FIG. 2. Patient 200 is placed on a table 310 designed to accommodate a focussed ultrasound transducer 330 in an ultrasound conducting liquid bath 320. The ultrasound conducting liquid chosen is one that will conduct ultrasonic energy with little attenuation. The ultrasound transducer 330 is moved inside the bore of static field magnets 260, 270 by positioner 70 to focus on different locations within patient 200. A path is computed by controller 100 under the direction of the operator from a set of images of the patient avoiding bone or air in the path of the ultrasound beam. The focal point of ultrasound transducer 330 is positioned by positioner 70 onto a tissue desired to be heated or destroyed, such as tumor 280 and pulsed to selectively heat tumor 280. The ultrasound transducer is interactively positioned by the operator while the operator views cross sectional temperature-sensitive images. (A more detailed description of the positioner is included in the aforementioned patent application Ser. No. 07/854,040).

Figure 3:
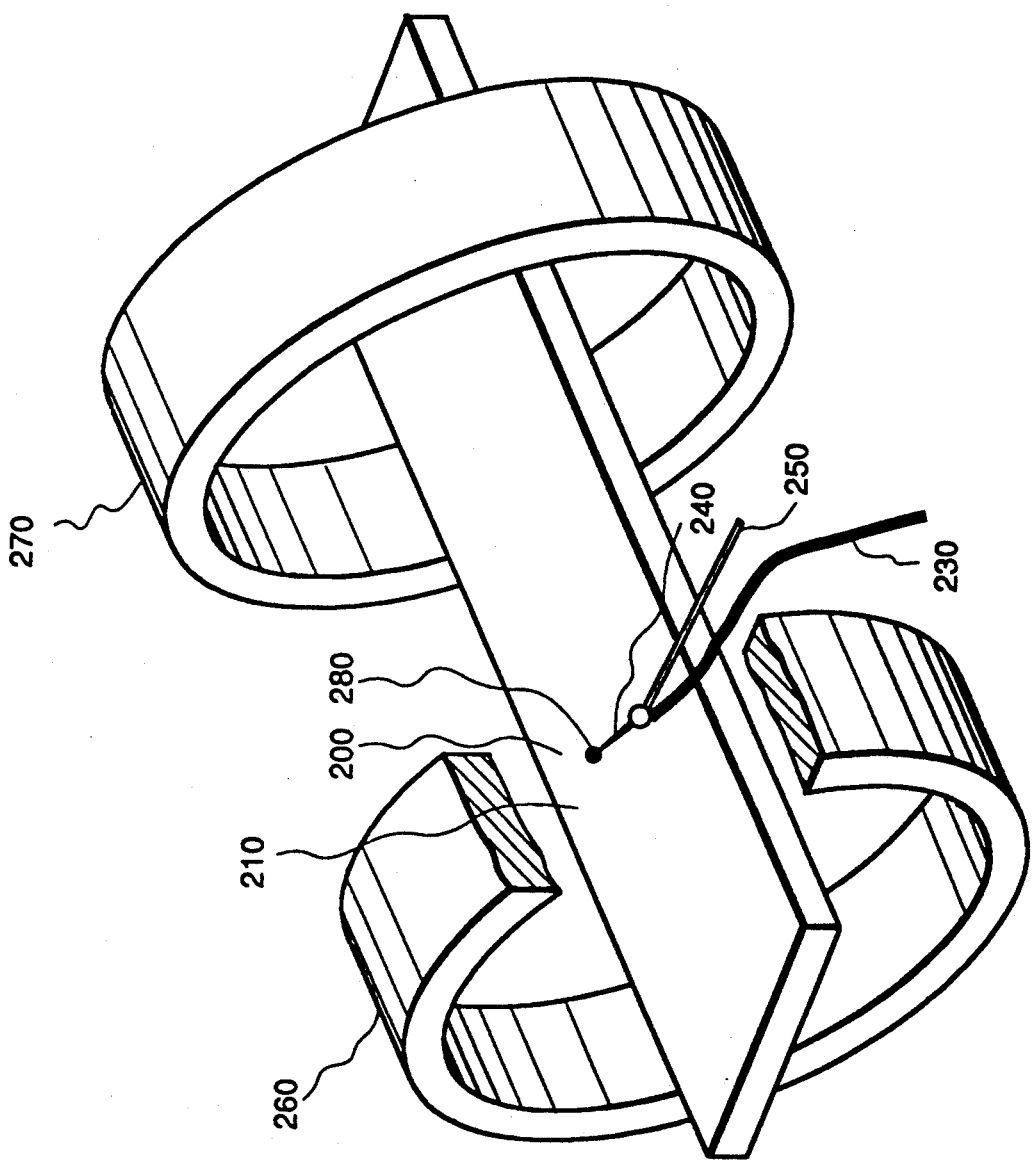
FIG. 3 is a partial illustration of a second embodiment of the present invention employing a laser source and fiber optics as a pulsed heat means with a patient positioned for surgery within the bore of the magnets.

Another embodiment employing a laser and optical fiber as pulsed heat means 80 is shown in FIG. 3. Patient 200 lies on a table 210 that moves into the bore of the two part static field magnet 260, 270. A laser fiber 230 is inserted into the patient with a hollow needle 240 which may optionally be guided by a mechanical positioning device 250 driven by the operator through controller 100 of FIG. 1. The trajectory of hollow needle 240 may be computed from conventional MR images of the patient which does not intersect critical anatomy such as large blood vessels. Heat is applied to tumor tissue 280 by periodically pulsing the laser through laser fiber 230 (i.e., a fiber optic material) to selectively destroy tumor 280 while the operator views a real-time temperature-sensitive MR image. More than one needle may be required to remove an irregularly shaped tumor.

Figure 4:
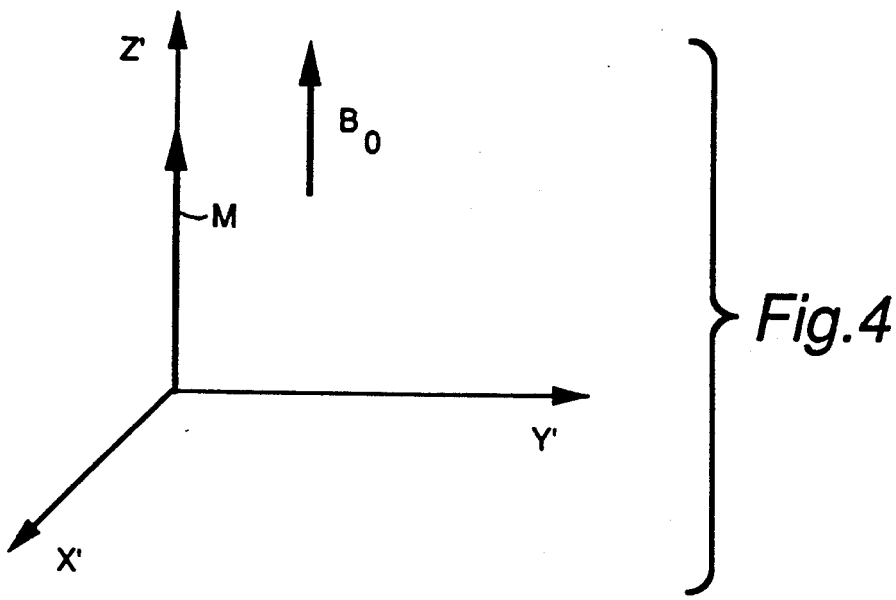
FIG. 4 is a representation of a bulk magnetization vector M, here equal to an equilibrium magnetization vector $M_0$ arising from unpaired resonant nuclei ("spins") within the tissue of a patient in a static magnetic field, shown in a reference frame X'Y'Z' rotating about the static magnetic field axis at a frequency equal to the precession frequency of the spins.

Free unpaired spinning protons ("spins") in the nucleus of a molecule of a specific tissue, normally hydrogen nuclei, align themselves in a magnetic field $B_0$ such that their axes precess about the magnetic field. Each spin is a small magnetic dipole. The net sum of the population of dipoles results in a bulk magnetization M which is aligned with static magnetic field $B_0$, shown in FIG. 4 in a reference frame X'Y'Z' rotating about the static magnetic field axis at a frequency equal to the precession of the spins. A radio frequency (RF) pulse applied in the presence of a magnetic field of predefined strength causes excitation or resonance of the spins, causing M to tip into the transverse plane X'Y', thereby increasing transverse magnetization vector $M_{x'y'}$ of the spins, as shown FIG. 5.

It is possible, by choosing the strengths of the RF pulse and magnetic field gradients, to selectively choose spins for excitation. Spatial localization of spins may be performed by choosing an RF pulse and magnetic field gradients to select spins of a specific desired area of the patient to be imaged.

Figure 7:
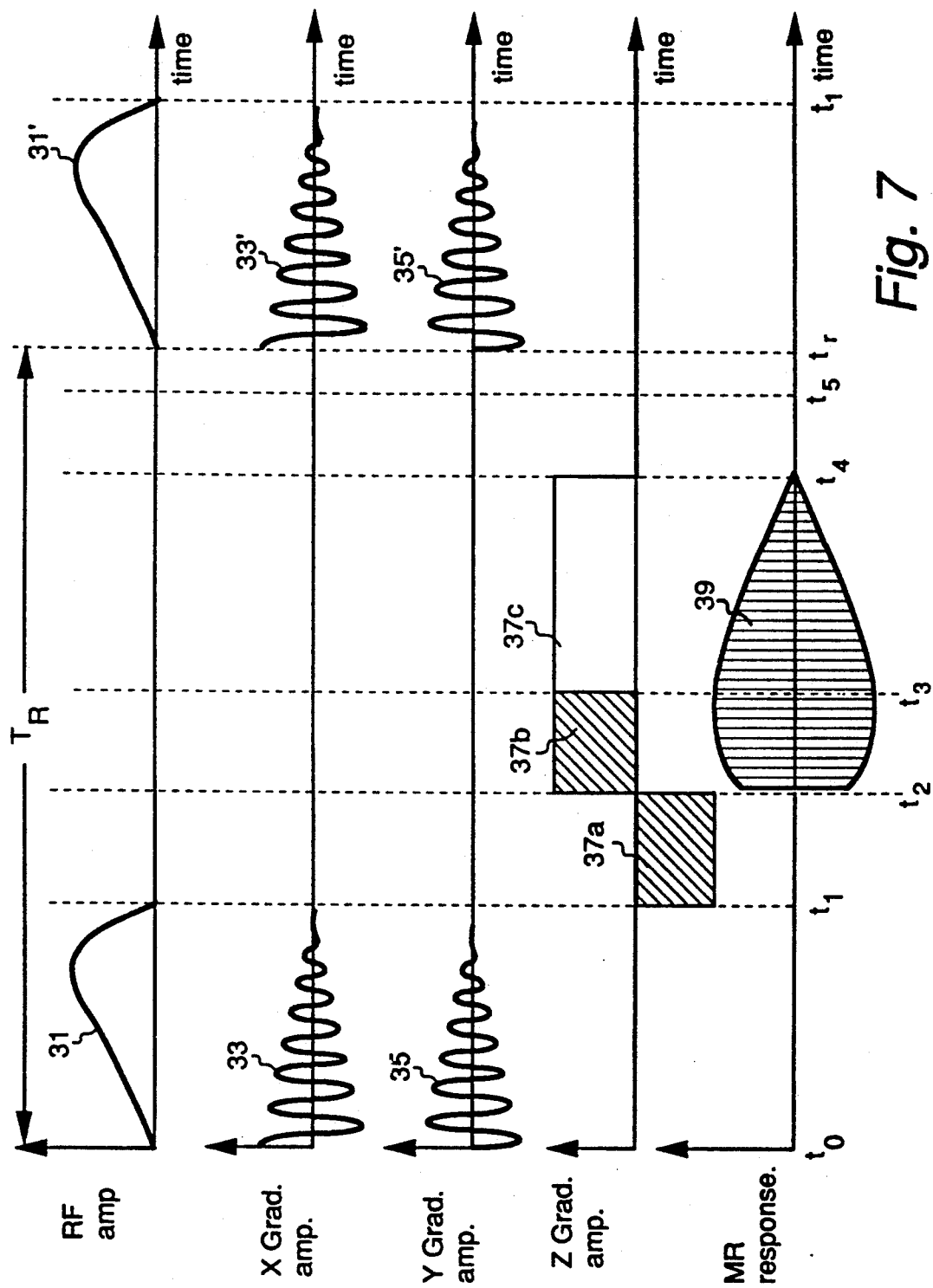
FIG. 7 is a cylindrical-selection $T_1$-weighted real-time temperature-sensitive MR pulse sequence according to the present invention.

The present invention achieves spatial excitation by either cylindrical-selection, or intersecting slice selection. In a first embodiment, a cylindrical region of the patient is excited or selected with RF pulse 31 and gradient pulses 33, 35 of "K" and "Y" directions, respectively, as shown in FIG. 7. The "Y" and "Y" directions pertain to two orthogonal directions, both perpendicular to the axis ("Z" direction) of the cylindrical excited region referred to as the logical coordinates. Logical coordinates may be converted to physical coordinates which are stationary with respect to physical objects, such as the MR imaging apparatus, by a conventional coordinate transformation. RF pulse 31 changes amplitude over time as the $G_x$ and $G_y$ orthogonal magnetic field gradients 33 and 35 create a resultant gradient field vector $G_r$ as shown in FIG. 6. The tip of vector $G_r$ traces a spiral path. The $G_x$ and $G_y$ orthogonal gradient waveforms 33, 35 and RF pulse 31 applied simultaneously, result in excitation of a cylindrical element of the patient. RF pulse 31 of FIG. 7 is chosen to be the weighted two-dimensional Fourier transform of the desired excitation profile. The method of determining gradient waveforms and RF pulses to excite desired shapes is disclosed in U.S. patent application "Sampling-Ring Saturation Pulse for Two-Dimensional Magnetic Resonance Selective Excitation" by Christopher J. Hardy, and Edward J. Nieters Ser. No. 07/928,390 filed Aug. 12, 1992, assigned to the present assignee and incorporated by reference.

After application of RF pulse 31 and magnetic field gradients 33, 35, excitation cylinder 81 has a transverse magnetization as indicated in FIGS. 8a and 8b. The center of cylinder 81 is at displacement $x_c$. At displacement $x_1$ of FIG. 8a, the transverse magnetization $M_{x'y'}$ increases to m, as shown in FIG. 8b. Transverse magnetization $M_{x'y'}$ remains substantially constant at m across the diameter of cylinder 81, which drops off at radius $x_2$ to zero.

Figure 5:
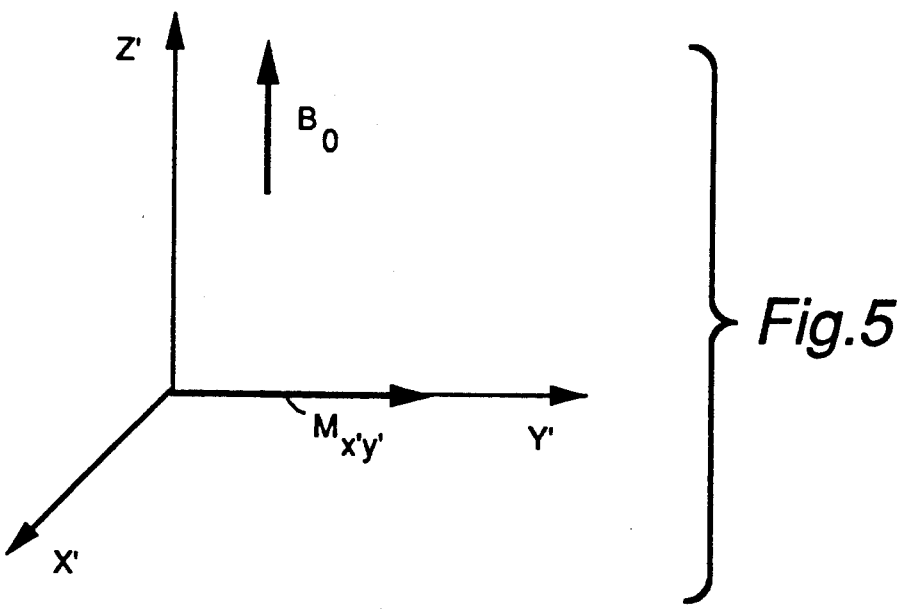
FIG. 5 is a representation of the bulk magnetization M of FIG. 4, also in reference frame X'Y'Z', after an MR excitation pulse is applied to tip it into the transverse plane X'Y', so that now the transverse component of magnetization $M_{X'Y'} = M$.

After the cylinder 81 is excited, transverse magnetization $M_{x'y'}$ of FIG. 5 precesses in the transverse plane. As shown in FIG. 7, a first portion 37a of readout gradient pulse 37 applied at time $t_1$ causes spins to become partially dephased such that spins are pointing in different directions within the transverse plane at any instant in time. A second portion 37b, essentially having the same size shaded area (the pulse duration multiplied by the gradient amplitude) of readout gradient pulse 37 applied at time $t_2$, causes spins to become rephased and peak at time $t_3$ creating a half-echo MR response signal 39. A last portion 37c of magnetic gradient pulse 37 causes the MR response signal to be encoded along the direction of gradient 37c. A longitudinal component $M_Z$ of magnetization, aligned along the static magnetic field $B_0$, is related to a spin-lattice relaxation time $T_1$ of the tissue by the following equation:

$$M_z = \begin{cases} M_0 & \text{for the first MR response signal} \\ M_0 \left(1 - e^{\frac{-TR}{T_1}}\right) & \text{for subsequent MR response signals} \end{cases} \quad [1]$$

where $M_0$ is the equilibrium longitudinal magnetization of the spins, and $T_R$ is the time before the next repetition of the pulse sequence. The longitudinal magnetization $M_Z$ grows toward the equilibrium value $M_0$ with a time constant $T_1$, which is affected by temperature. $T_1$ is increased in tissue by approximately 1% for each 1° C. change in temperature, due to thermal influences on spin-lattice interactions. RF excitation pulse 31' of subsequent repetitions tips $M_Z$ into the transverse plane, producing an MR response signal $M_{sig}$ which is indicative of temperature of the tissue in the excited region. A one-dimensional Fourier Transform (1 DFT) is applied to the MR response signal to determine the amplitude of the AM response signal for each frequency, which is mapped to each location along the readout gradient, thereby producing a temperature-sensitive profile along the direction of the readout gradient.

This entire pulse sequence is repeated after time $T_R$, starting with RF pulse 31' and gradient pulses 33' and 35'.

Figure 9:
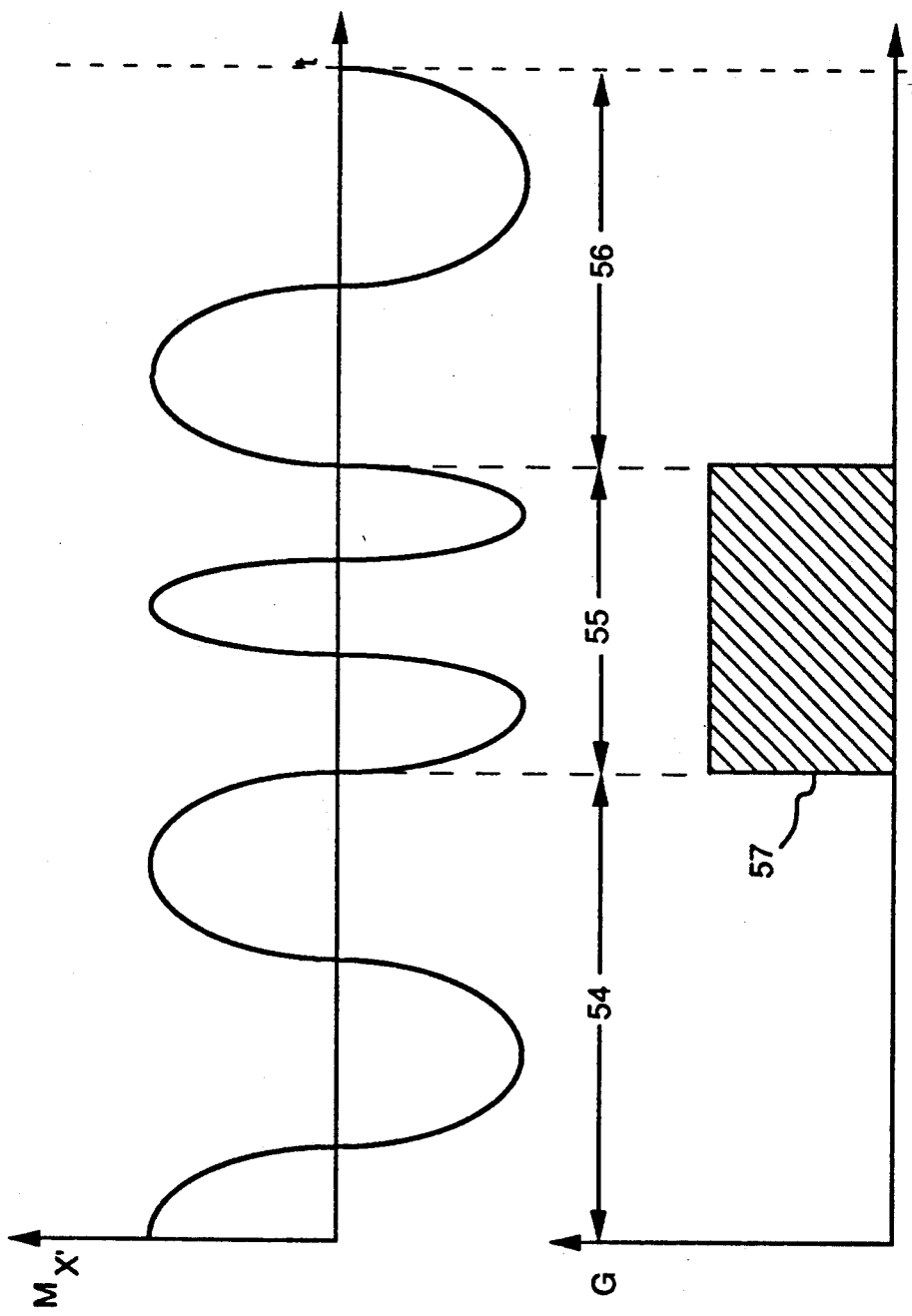
FIG. 9 is an illustration of an "X'" component of the bulk magnetization vector M in the rotating frame of FIG. 5 during an applied magnetic field gradient.

In a second embodiment of the invention, diffusion sensitivity is encoded. FIG. 9 is an amplitude vs. time diagram of the "X'" component $M_{X'}$ of the bulk magnetization M at a single location, being a component of the total transverse magnetization vector $M_{x'y'}$ of FIG. 5 within a tissue. The vector M rotates at a specific constant frequency during period 54 related to the magnetic field experienced by the spins. A magnetic field gradient 57 having an amplitude G is applied during period 55, changing the magnetic field experienced by the spins, thereby changing the frequency of the rotation of the bulk magnetization vector M. During period 56 of FIG. 9, M reverts back to its original frequency, but the phase has been increased. This is known as phase evolution.

The relative phase evolution of the transverse magnetization vector $M_{x'y'}$ of FIG. 5 at each point in space is determined by the deviation in magnetic field from value B0 at that point (which is in turn determined by the amplitude of the applied gradient) and the time during which it is applied. The relative phase shift of the transverse magnetization arising from stationary spins is directly proportional to the lobe area under magnetic field gradient pulse 57.

By applying a gradient to a group of moving spins, causing phase evolution in one sense, followed by application of another gradient, causing phase evolution in an opposite sense, a net phase evolution may be encoded indicating the motion of the spins. This phase shift, $\phi$(motion), may be described as:

$$\phi_{(motion)} = \gamma V T A_g \quad [2]$$

where $\gamma$ is the gyromagnetic ratio specific to a given element, V is a component of the spins' velocity parallel to the direction of the applied gradients, T is the time between the centers of the magnetic gradient pulses applied along the line in which flow is to be measured, and $A_g$ is the area (gradient strength multiplied by duration of its application). Equation [2] ignores phase shifts which can arise from higher orders of motion such as acceleration, and change in acceleration, etc.

Since diffusion is motion of spins, and temperature has a direct relation to the rate of diffusion, diffusion encoding of the type described above may be employed in measuring temperature.

Figure 10:
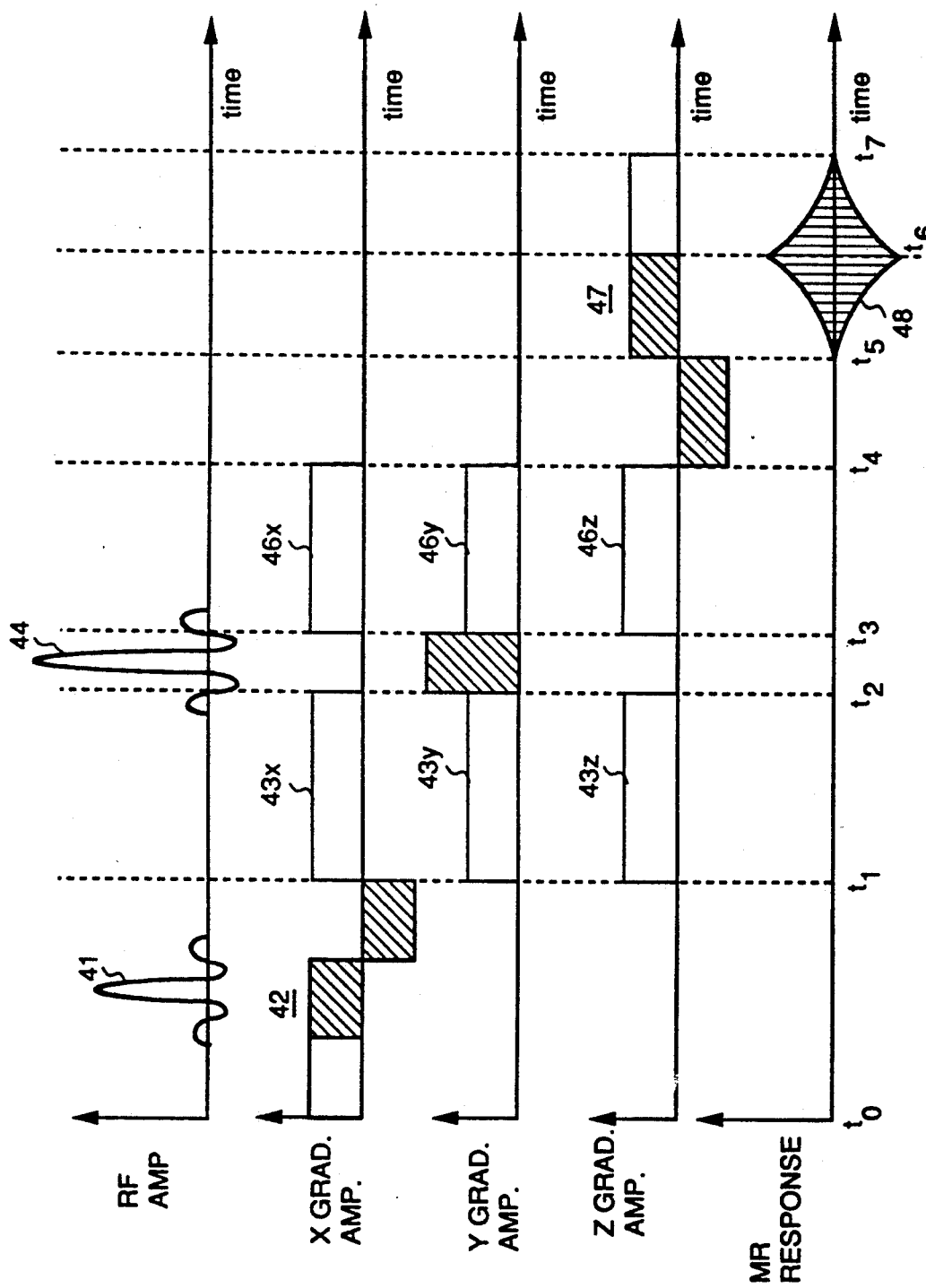
FIG. 10 is a timing diagram of an intersecting slice selection and diffusion gradient encoded real-time temperature-sensitive MR pulse sequence according to the present invention.

FIG. 10 illustrates a second embodiment of the real-time temperature-sensitive AM pulse sequence of the present invention employing intersecting slice selection and diffusion gradient encoding. An RF sine(x)/x ("sinc") pulse 41 is applied simultaneously with an X magnetic field gradient pulse 42 causing spins to nutate until they are oriented in the transverse plane (a 90° pulse). Cross-hatched portions of pulse 42 are of equal areas above and below the axis. Sinc pulse 41 transforms in a frequency domain into a narrow band square region from encompassing a small frequency range. Application of RF sinc pulse 41 with gradient pulse 42 has the effect of exciting a narrow slice of spins of the patient in the logical Y,Z plane precessing at corresponding frequencies. Diffusion gradients 43x, 43y, 43z are applied to cause phase evolution in a forward sense.

A RF refocussing pulse 44 acts to reverse the relative phase of each of the spins. If a spin has gained 80° of forward phase evolution during application of the diffusion gradient, then after the application of RF refocussing pulse 44, the same spin now has a −80° phase, or $\phi = -\phi$.

Figure 11:
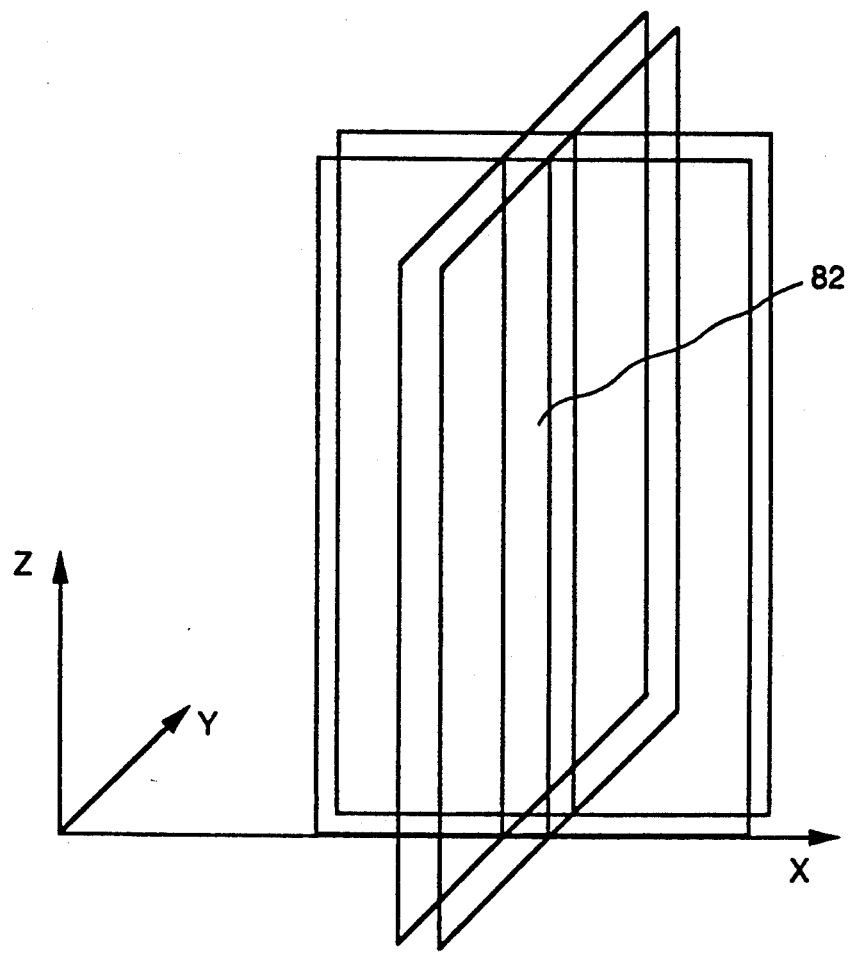
FIG. 11 is an illustration of the intersection of two imaginary slices according to the present invention.

A Y magnetic field gradient is applied simultaneously with RF refocussing pulse 44 to select a region, that region being the intersection of a slice in the X,Z plane and the first selected slice of tissue in the Y,Z plane shown as rod-shaped excitation region 82 in FIG. 11.

A second set of diffusion gradients 46x, 46y, 46z is applied along the X, Y, Z directions respectively causing another forward phase evolution. Since RF refocussing pulse 44 has flipped each phase to its negative value, a forward phase evolution will cause stationary spins to become rephased at time $t_4$. Moving spins will be phase encoded by the amount of diffusion in the direction of the net gradient, indicative of the temperature. A readout magnetic field gradient pulse 47 oriented along the length of rod 82 of FIG. 11 (Z axis) encodes a full echo MR response signal 58 radiated by rod 82 which peaks at time $t_6$. Cross-hatched portions of pulse 47 have equal areas under the curve. This results in a temperature-sensitive profile through rod 82 which may be interactively reoriented.

Figure 12:
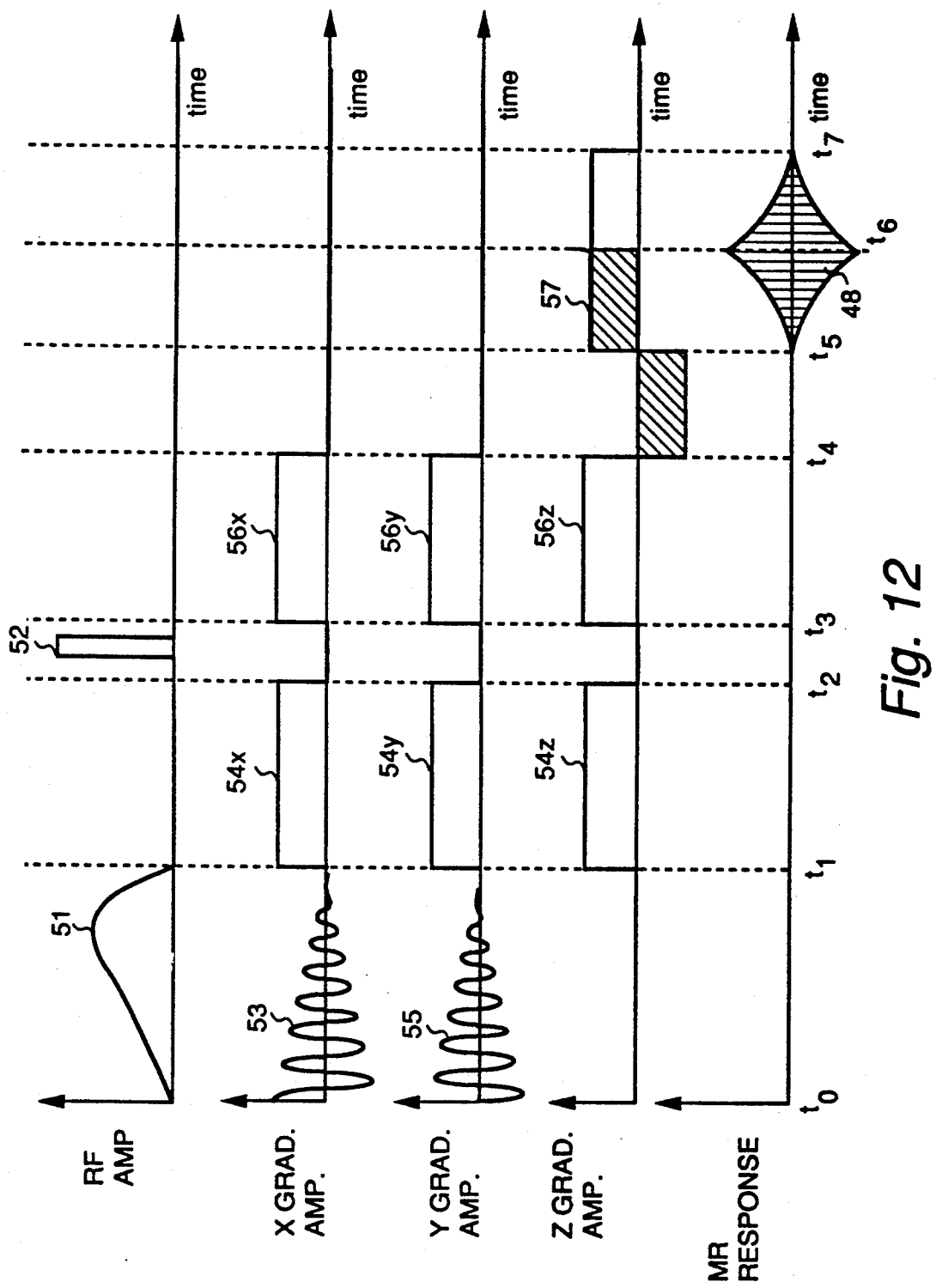
FIG. 12 is a cylindrical-selection diffusion gradient encoded real-time temperature-sensitive MR pulse sequence according to the present invention.

FIG. 12 illustrates a third embodiment of the real-time temperature-sensitive MR pulse sequence employing cylindrical excitation and diffusion gradient temperature coding. Two orthogonal time varying magnetic field gradients 53, 55 and an RF excitation pulse 51 are applied simultaneously to excite a cylinder of tissue within the patient similar to the excitation of tissue described in conjunction with FIG. 7.

Simultaneous diffusion gradients are applied in the X,Y,Z, directions 54k, 54y, 54z respectively. An RF refocussing pulse 52 is applied. A second set of diffusion gradients 56x, 56y, 56z are then applied along the X,Y,Z, directions, respectively. An MR response signal is then acquired in the presence of a readout gradient 57 oriented along the length of the cylinder. A one-dimensional Fourier Transform (1 DFT) is applied to the MR response signal resulting in a temperature-sensitive profile along the direction of readout magnetic field gradient from magnetic field gradient pulse 57. Cross-hatched areas of pulse 57 have equal area above and below the axis. In this manner a temperature-sensitive profile through the specific tissue along the axis of the cylindrical excitation region may be recorded once every 50 msec or less.

The cylinder axis can be oriented in an arbitrary direction by proper mixing of the X,Y, and Z magnetic field gradients. In addition, the cylinder can be offset from the center of the magnet to any specified location by frequency modulation of the RF waveform of the excitation pulse as described in "Off-Axis Spatial Localization with Frequency Modulated Nuclear Magnetic Resonance Rotating (ρ) Pulses" by C. J. Hardy, P. A. Bottomley, P. B. Roemer, J. Appl. Phys. 63, 4741 (1988), which is hereby incorporated by reference.

EXPERIMENTAL RESULTS

Experiments indicate that when a laser which emits in the infrared range of approximately 10W power is used to irradiate brain tissue for several minutes, a number of distinct regions of tissue damage arise. Cells nearest the end of the fiber optic, which experience temperatures >160° F., suffer instant damage and death. Those in the immediately surrounding regions, which reach temperatures >140°, are also damaged irreparably, but with cell death occurring more slowly. In both of these cases the changes are readily seen as regions of decreased intensity in an MR image. Cells that are heated to temperatures somewhat lower than 140° also experience changes leading to reduced intensity in the MR image, but in this case the changes are reversible, with recovery to a normal MR intensity as the cell cools back down. It is obviously very important that the operator is able to distinguish between the second and third types of change. Nearby vasculature in the brain acts as a sort of radiator, providing differing degrees of cooling to different regions depending on the specific geometry. Therefore, it is important to have a means of real-time monitoring of the healing process.

A surgical procedure would involve irradiating the specific tissue (e.g. tumor) until the region of reduced intensity in the temperature-sensitive profile roughly matched the boundaries of the tumor. The cylindrical or rod-shaped excitation region could be reoriented interactively to probe the tumor in all three dimensions. A delay allowing recovery to thermal equilibrium, again monitored by the MR temperature-sensitive real-time MR pulse sequence, would reveal those areas on the border which were not irreversibly damaged. The tumor would then undergo additional irradiation, perhaps with several iterations of irradiation and recovery, until the border regions were destroyed as well. In this way the amount of damage to surrounding normal tissue would be minimized.

Figure 13A:
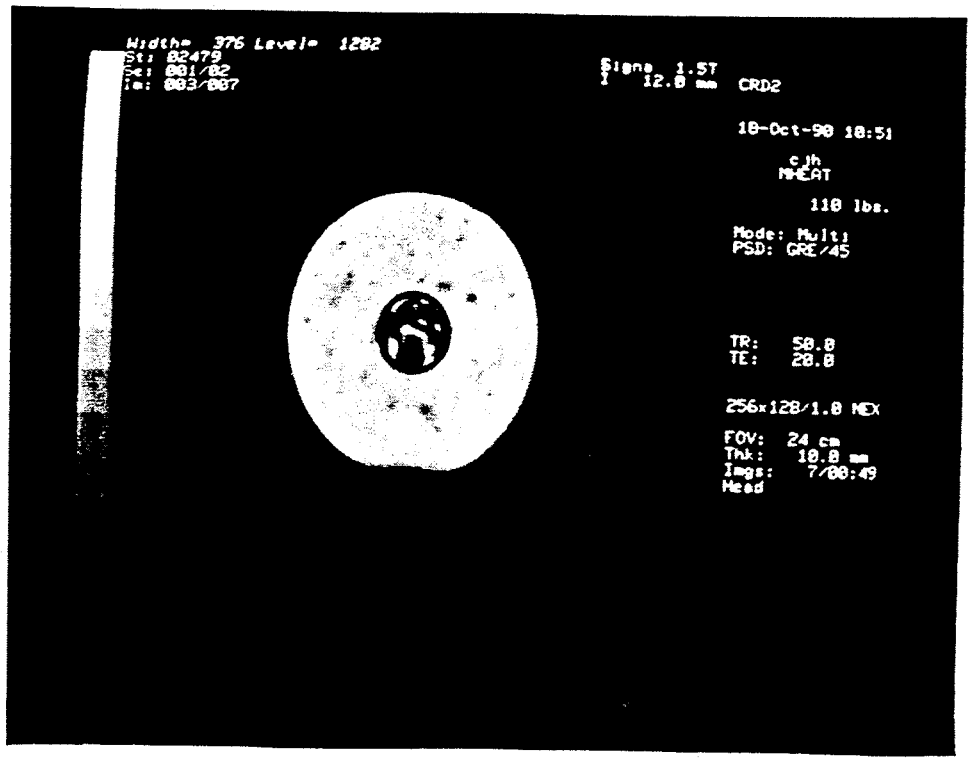
FIG. 13a is an axial MR image of an agarose gel phantom surrounding a tube of cold water.
Figure 13B:
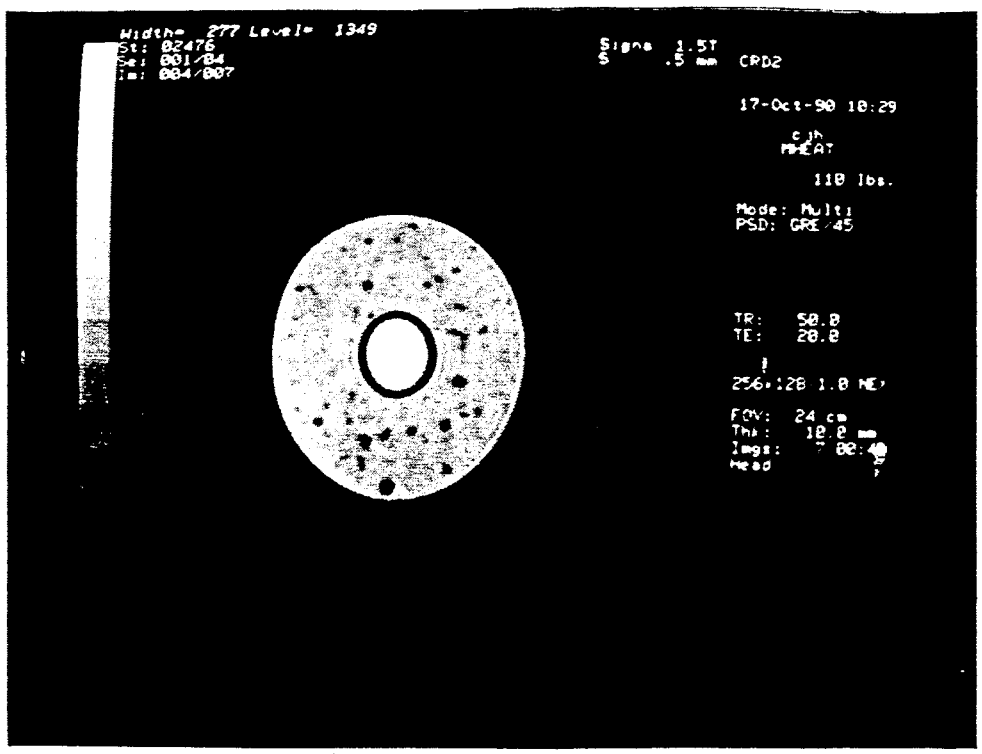
FIG. 13b is an axial MR image of the same agarose gel phantom of FIG. 13a surrounding a tube of hot water.

The present invention was employed on a phantom for real-time monitoring of laser surgery on a standard SIGNA ® MR diagnostic system. The pulse sequence employed is that of FIG. 7. FIGS. 13a and 13b are axial MR images of the same agarose phantom surrounding a tube of water but acquired at two different temperatures. The water is circulated from a heat bath using a peristaltic pump, and maintained at constant temperature. The two dark spots in FIG. 13a show the locations of two thermocouple wires used to measure the temperature in the agarose. Temperature profiling of the present invention was performed in a region just superior to the region containing the wires.

Figure 13C:
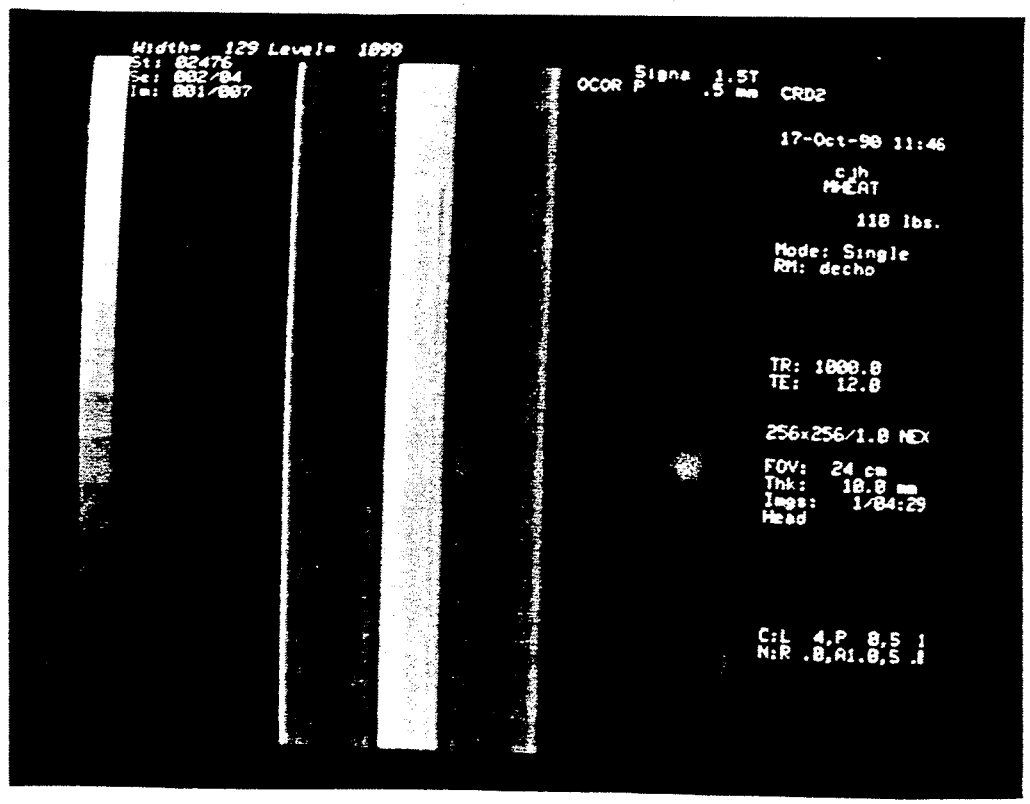
FIG. 13c and 13d is an image of a series of temperature vs. position graphs, temperature-sensitive profiles, of the phantoms of FIGS. 13a, 13b, respectively.
Figure 13D:
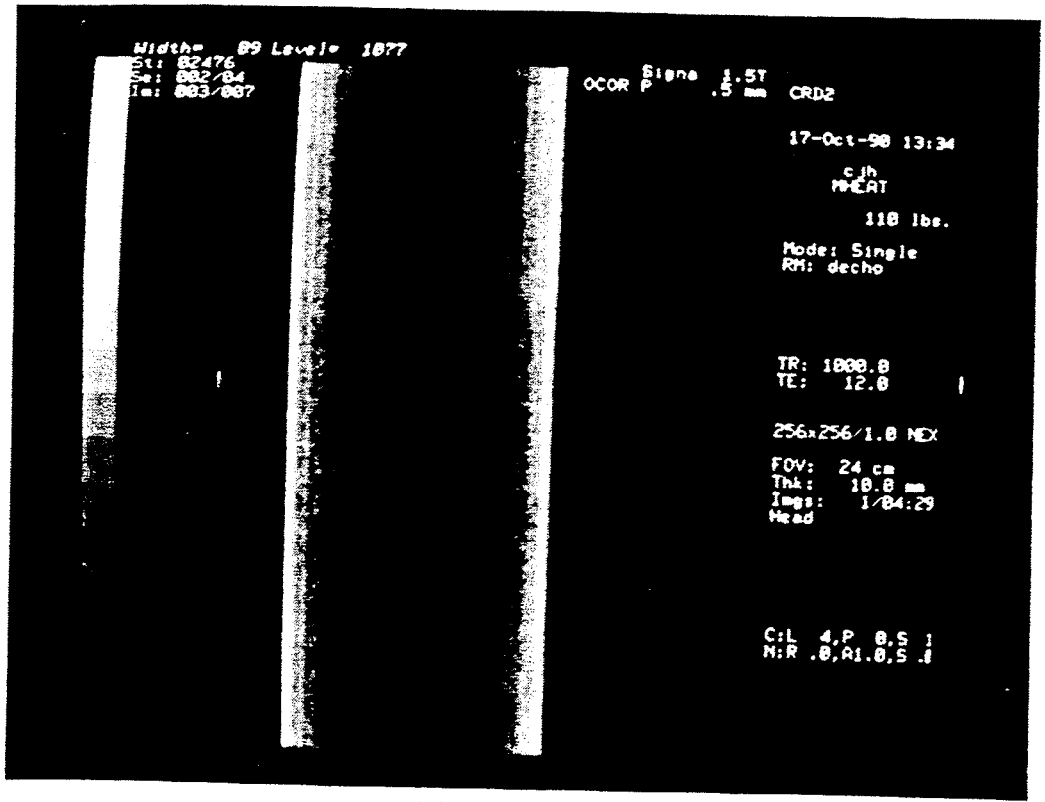

FIGS. 13c and 13d are temperature-sensitive profiles taken through the center of the phantom shown in FIGS. 13a, 13b, respectively, as a function of time, with time running from top to bottom. Data for each temperature-sensitive profile was acquired in 100 msec, with approximately 256 temperature-sensitive profiles taken. FIG. 13c was acquired at room temperature (22.3° C). In FIG. 13d, the thermocouple just outside the inner tube read 41.6 C and the outer thermocouple read 25.9 C.

Figure 13E:
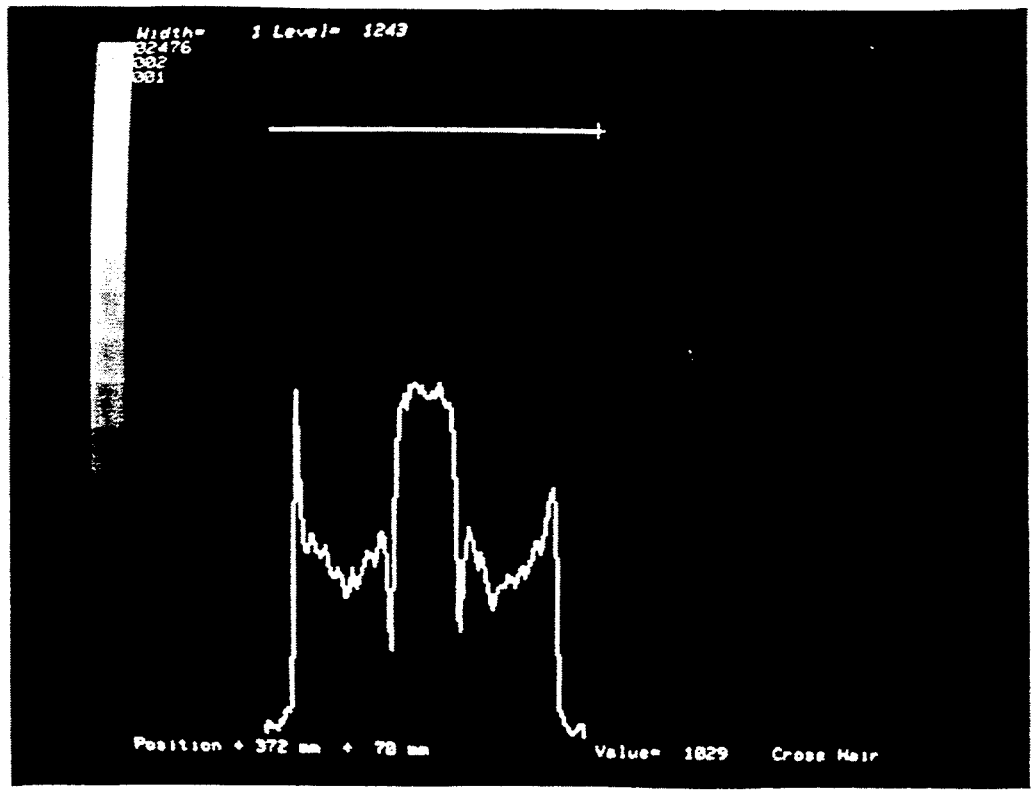
FIG. 13e is a temperature vs. position graph of a single temperature-sensitive profile of FIG. 13c.
Figure 13F:
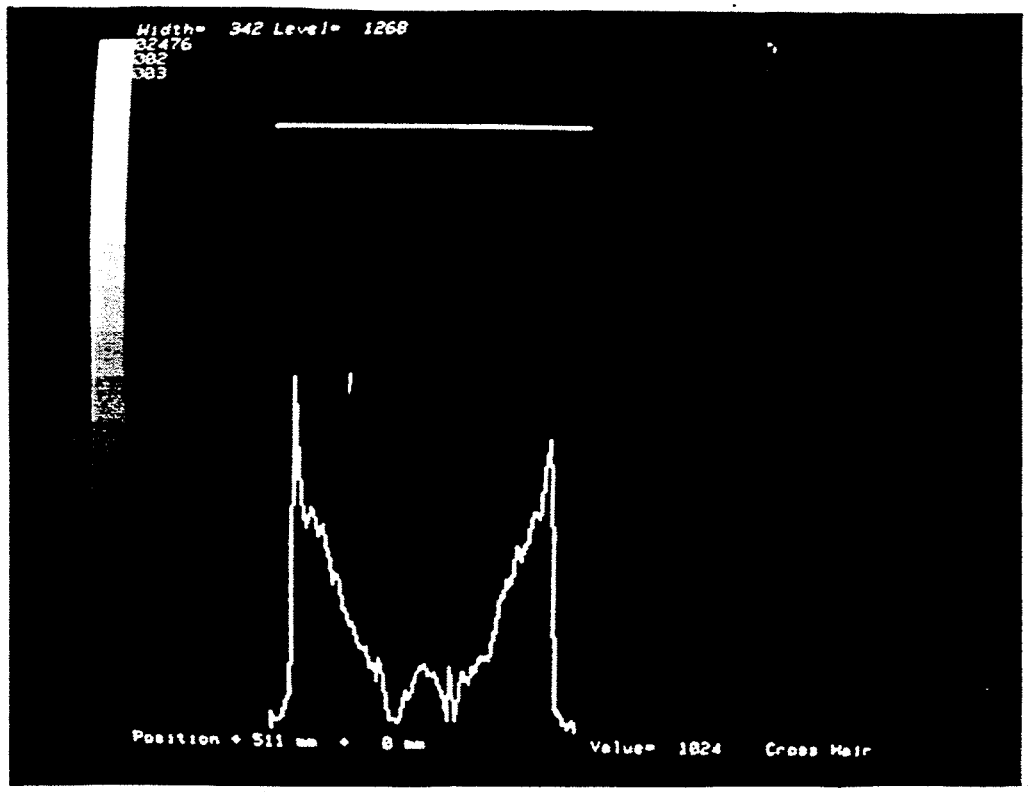
FIG. 13f is a temperature vs. position graph of a single temperature-sensitive profile of FIG. 13d.

FIGS. 13e and 13f are individual temperature vs. position profiles taken from FIGS. 13c and 13d, respectively. The most striking effect of elevated temperature is the drastic drop in signal in the inner tube, presumably caused by convection in the water. In addition, there is signal loss in the agarose which varies with distance from the hot inner tube.

Figure 14A:
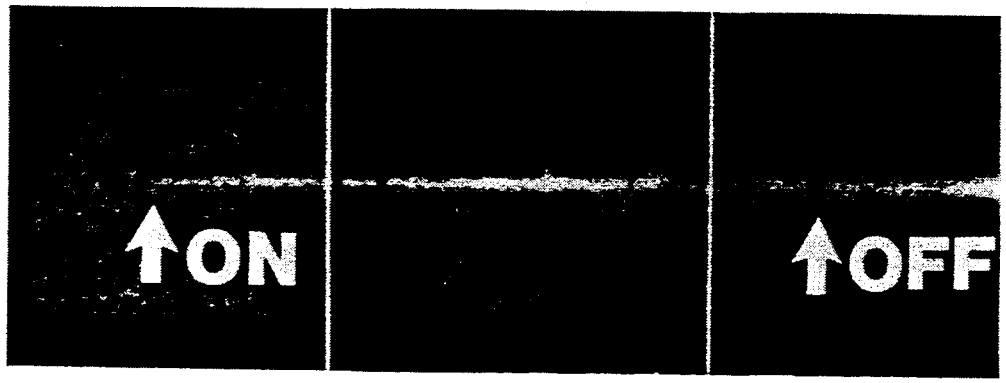
FIG. 14a is a position vs. time temperature-sensitive image acquired with the present invention of the focal point of a focussed ultrasound pulsed heat means of the present invention.
Figure 14B:
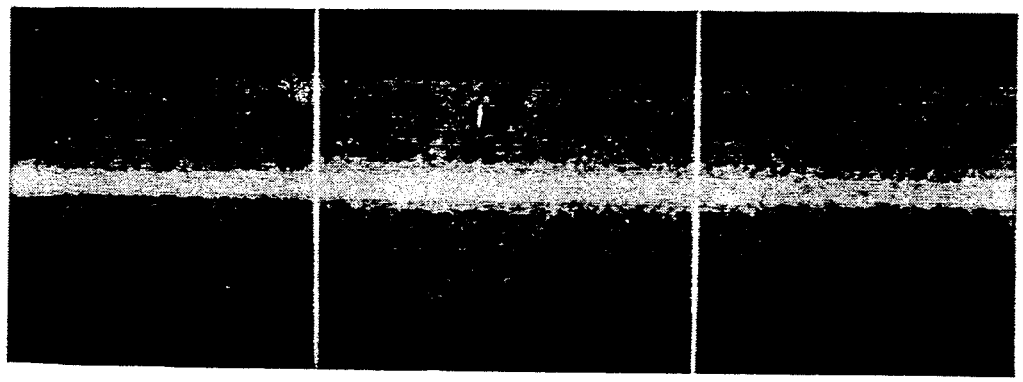

FIGS. 14a and 14b illustrate the focussed ultrasound embodiment of the present invention used to heat and monitor a gel phantom. Here, the excitation cylinder has been oriented to pass through the ultrasonic transducer's focal point, orthogonal to the ultrasound beam. The time aids runs from left to right and the vertical aids represents the position along the excitation cylinder. The ultrasound beam was turned on and off as indicated in FIG. 14a. Rapid heating is evident at the focal point, followed by diffusion of the heat and then further diffusion and cooling after the beam is turned off as shown in FIG. 14b. FIG. 14b was acquired immediately after FIG. 14a.

By employing MR temperature-sensitive pulse sequences according to the present invention, temperature can be monitored with time resolution as low as 30 msec. The present invention, therefore, is a viable means of performing heat surgery accurately and effectively.

While several presently preferred embodiments of the invention have been described in detail herein, many modifications and variations will now become apparent to those skilled in the art. It is, therefore, to be understood that the appended claims are intended to cover all such modifications and variations as fall within the true spirit of the invention.

What is claimed is:

1. A magnetic resonance (MR) pulsed heat system for allowing an operator to selectively heat tissue within a patient comprising:
   a) pulsed heat-producing means adapted for concentrating energy at an application point;
   b) positioning means for positioning the application point of the pulsed heat-producing means in a specific tissue within the patient so as to create a heated region within the specified tissue;
   c) operator responsive control means for enabling said operator to control the positioning means;
   d) an MR imaging means comprising:
      1. a radiofrequency (RF) transmitter for transmitting an RF sine(x)/x "sinc" selection pulse and a 180° RF sinc refocussing pulse into said patient;
      2. a gradient means for
         i. creating a slice selection magnetic field gradient along an "X" direction simultaneously with application of the RF sinc selection pulse to cause excitation of a first slice of tissue within said patient,
         ii. applying a first set of diffusion gradients in the "X" direction, and in the "Y" and "Z" directions orthogonal to the "X" direction after selection of the first slice and before application of the 180° RF sinc refocussing pulse to cause a phase evolution of a plurality of nuclear spins in said patient;
         iii. creating a second slice selection magnetic field gradient simultaneously with application of the 180° RF sinc refocussing pulse to cause phase reversal only within a second slice of tissue within said patient intersecting the first slice, thereby creating a rod-shaped region of excited nuclear spins with reversed phase,
         iv. applying a second set of diffusion gradients in the "X", "Y" and "Z" directions after application of the 180° RF since refocussing pulse to cause a second phase evolution of the nuclear spins, thereby encoding diffusion of the nuclear spins in the excitation region, and
         v. applying a readout gradient to said rod-shaped excitation region along the length of the excitation region being the "Z" direction for which a temperature-sensitive profile desired;
      3. receiver means for receiving an MR response signal from the rod-shaped excitation region; and
      4. computation means for computing a temperature vs. position profile along the readout gradient from the MR response signal received from the receiver means, thereby creating real-time temperature-sensitive MR images of the heated region; and e) display means for displaying the temperature-sensitive images to said operator.

2. The MR pulsed heat system system of claim 1 wherein the pulsed heat-producing means comprises:
a) a source of pulsed optical energy;
b) an invasive device adapted for insertion into the patient to reach the specific tissue of the patient; and
c) an optical fiber having an external end and an internal end adapted to be fitted into the invasive device with its internal end within the specific tissue, the fiber being adapted to pass the optical energy from the pulsed optical energy source into the external end, to its application point in the specific tissue adjacent the internal end.

3. The MR pulsed heat system system of claim 2 wherein the source of pulsed optical energy comprises a laser.

4. The MR pulsed heat system system of claim 1 wherein the pulsed heat-producing means comprises:
an ultrasonic transducer adapted to generating pulsed ultrasonic energy concentrated at a focal point, the focal point being the application point.

5. The method of performing heat surgery on a patient as guided by magnetic resonance (MR) imaging comprising, the steps of:
a) creating an internal image of tissues of said patient;
b) determining the position of a specified tissue in the patient;
c) applying pulsed heat at a predetermined pulse frequency to the specified tissue to create a heated region within the specified tissue;
d) monitoring the heated region with an MR imaging means by;
   1. transmitting an RF sine(x)/x "sinc" selection pulse into said patient;
   2. applying a slice selection magnetic field gradient along an "X" direction simultaneously with application of the RF sinc selection pulse to cause excitation of a first slice of tissue within said patient;
   3. applying a first set of diffusion gradients in the "X" direction, and a "Y" and "Z" direction orthogonal to the "X" direction to cause a phase evolution of a plurality of nuclear spins in the first slice of said patient;
   4. transmitting a 180° RF sinc refocussing pulse into said patient reversing the phase of the nuclear spins;
   5. applying a second slice selection magnetic field gradient simultaneously with the application of the 180° RF sinc refocussing pulse causing excitation of a second slice of tissue within said patient intersecting the first slice and thereby create a rod-shaped excitation region;
   6. applying a second set of diffusion gradients in the "X", "Y" and "Z" directions after application of the 180° RF sinc refocussing pulse to cause a second phase evolution of the nuclear spins and thereby encode diffusion of the nuclear spins;
   7. applying a readout gradient to the rod-shaped excitation region along the length of the excitation region, the rod-shaped excitation region being along the "Z" direction for which a temperature-sensitive profile is desired;
   8. receiving an MR response signal from the rod-shaped excitation region; and
   9. computing a temperature vs. position profile along the readout gradient from the MR response signal; and
e) adjusting the frequency and the position of the heated region so as to heat the specified tissue without substantial injury to adjacent tissue.

6. The method of performing heat surgery on a patient of claim 5 wherein the step of applying pulsed heat comprises the steps of:
a) focussing ultrasonic waves on an application point; and
b) positioning the application point at a predetermined location within the specific tissue.

7. The method of performing heat surgery on a patient of claim 5 wherein the step of applying pulsed heat comprises the steps of:
a) creating optical energy; and
b) passing the optical energy through an optical fiber to a predetermined application point within the specific tissue.

* * * * *